US009838875B2

(12) United States Patent
Yumoto et al.

(10) Patent No.: US 9,838,875 B2
(45) Date of Patent: Dec. 5, 2017

(54) MOBILE TERMINAL DEVICE, INFORMATION MANAGEMENT DEVICE, AND INFORMATION MANAGEMENT SYSTEM

(71) Applicant: OLYMPUS CORPORATION, Hachioji-shi, Tokyo (JP)

(72) Inventors: Kenta Yumoto, Hachioji (JP); Osamu Tokita, Hachioji (JP); Hiroaki Miura, Hachioji (JP); Takafumi Onishi, Chofu (JP); Masaomi Tomizawa, Hachioji (JP); Osamu Nonaka, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/177,990

(22) Filed: Jun. 9, 2016

(65) Prior Publication Data
US 2016/0295415 A1 Oct. 6, 2016

Related U.S. Application Data

(63) Continuation of application No. PCT/JP2015/072537, filed on Aug. 7, 2015.

(30) Foreign Application Priority Data

Jan. 22, 2015 (JP) ................................ 2015-010506

(51) Int. Cl.
*H04M 1/66* (2006.01)
*H04M 1/68* (2006.01)
(Continued)

(52) U.S. Cl.
CPC ............ *H04W 12/08* (2013.01); *G06F 21/00* (2013.01); *G06F 21/60* (2013.01); *G06Q 50/24* (2013.01);
(Continued)

(58) Field of Classification Search
CPC ....... H04W 12/08; H04W 88/02; G06F 21/60; G06F 21/00; H04M 1/67; H04M 1/72577;
(Continued)

(56) References Cited

U.S. PATENT DOCUMENTS

| 6,212,410 B1 | 4/2001 | Ishida |
| 2005/0266885 A1* | 12/2005 | Katayanagi ......... H04L 63/0853 455/558 |

(Continued)

FOREIGN PATENT DOCUMENTS

| JP | 10-42035 A | 2/1998 |
| JP | 10-243089 A | 9/1998 |

(Continued)

OTHER PUBLICATIONS

International Search Report and Written Opinion mailed in corresponding International Patent Application No. PCT/JP2015/072537 dated Oct. 27, 2015, consisting of 7 pp.

(Continued)

*Primary Examiner* — Ajit Patel
(74) *Attorney, Agent, or Firm* — Volpe and Koenig, P.C.

(57) ABSTRACT

According to the present invention, a mobile terminal device includes: an operation input section which accepts operations; a memory section which previously stores a list of states of the mobile terminal device during use as locking conditions to determine a state at the time of limiting an operation of the mobile terminal device; a state determining section which generates state information in accordance with a state of the mobile terminal device; and a function limiting section which determines whether the state information meets the locking conditions, and switches the mobile terminal device to a locked state to limit an operation of the operation input section, when the state information is determined to meet the locking conditions.

9 Claims, 7 Drawing Sheets

15F0367P

(51) Int. Cl.
*H04M 3/16* (2006.01)
*H04W 12/08* (2009.01)
*G06F 21/00* (2013.01)
*G06Q 50/24* (2012.01)
*H04M 11/00* (2006.01)
*H04M 1/67* (2006.01)
*G06F 21/60* (2013.01)
*H04M 1/725* (2006.01)
*H04W 88/02* (2009.01)

(52) U.S. Cl.
CPC ......... *H04M 1/67* (2013.01); *H04M 1/72577* (2013.01); *H04M 11/00* (2013.01); *H04M 1/72527* (2013.01); *H04W 88/02* (2013.01)

(58) Field of Classification Search
CPC ... H04M 11/00; H04M 1/72527; G06Q 50/24
See application file for complete search history.

(56) References Cited

U.S. PATENT DOCUMENTS

| | | | | |
|---|---|---|---|---|
| 2015/0079943 | A1* | 3/2015 | Williams | H04W 12/08 455/411 |
| 2015/0237195 | A1* | 8/2015 | Jones | H04M 1/72577 455/418 |
| 2015/0296371 | A1* | 10/2015 | Kong | H04W 8/18 455/419 |
| 2015/0381798 | A1* | 12/2015 | Yoon | H04M 1/72577 455/411 |
| 2016/0205238 | A1* | 7/2016 | Abramson | G01C 21/3484 455/456.4 |

FOREIGN PATENT DOCUMENTS

| | | | | |
|---|---|---|---|---|
| JP | 2003-289352 | A | | 10/2003 |
| JP | 2005-340976 | A | | 12/2005 |
| JP | 2006-031517 | A | | 2/2006 |
| JP | 2007-013546 | A | | 1/2007 |
| JP | 2007-013630 | A | | 1/2007 |
| JP | 2007013546 | A | * | 1/2007 |
| JP | 2010-022062 | A | | 1/2010 |
| JP | 2012-085121 | A | | 4/2012 |
| JP | 2013-080997 | A | | 5/2013 |
| JP | 2013080997 | A | * | 5/2013 |
| JP | 2013-168725 | A | | 8/2013 |
| JP | 2013-207802 | A | | 10/2013 |
| JP | 2014-179872 | A | | 9/2014 |
| JP | 2014179872 | A | * | 9/2014 |

OTHER PUBLICATIONS

English Translation of International Search Report mailed in corresponding International Patent Application No. PCT/JP2015/072537 dated Oct. 27, 2015, consisting of 2 pp.

Office Action mailed in corresponding Japanese Patent Application No. 2015-559335 dated Feb. 28, 2017 consisting of 6 pp. (English Translation Provided).

* cited by examiner

15F0367P
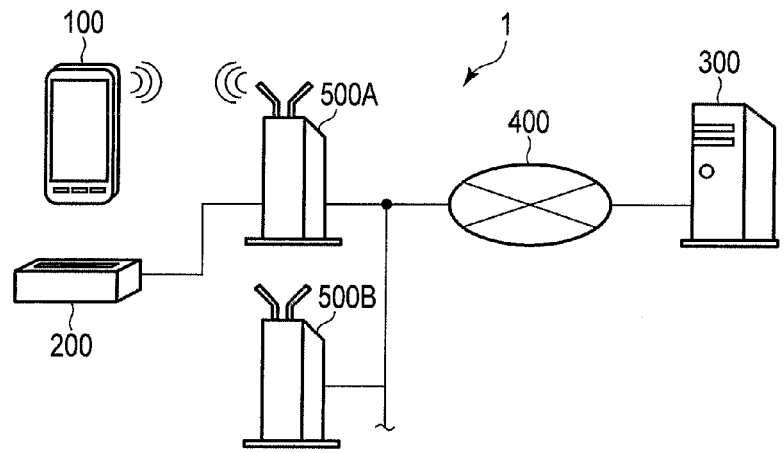
FIG. 1
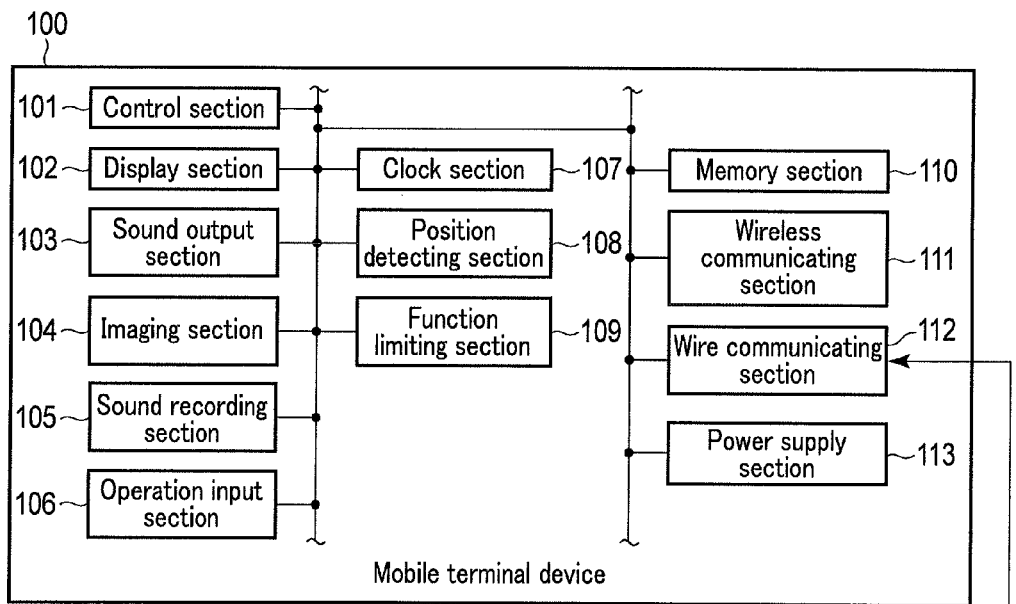
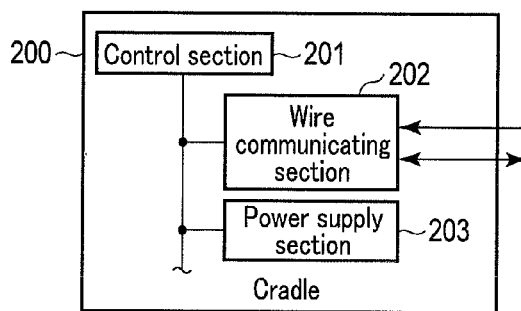
FIG. 2

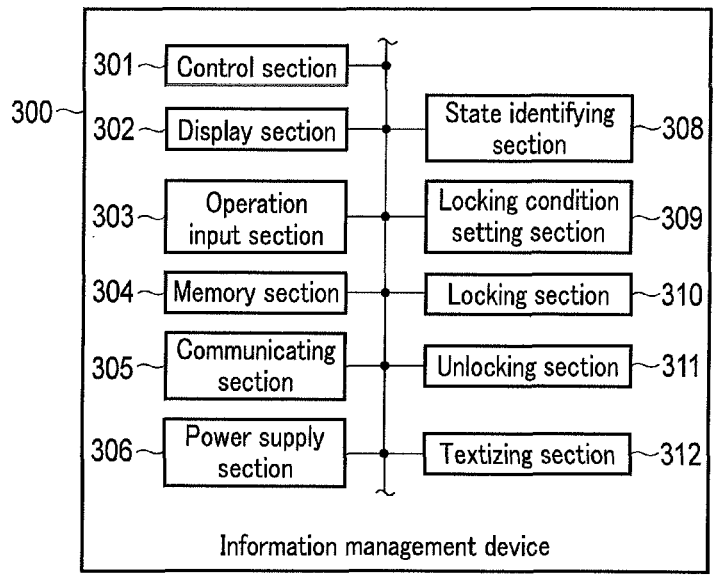

FIG. 3

| Enabled/Disabled | Locking conditions |
|---|---|
| Enabled | Connection to cradle was not established for predetermined time |
| Enabled | Charging was not performed for predetermined time |
| Enabled | Traveling in route other than predetermine route was performed |
| Enabled | Use in place other than predetermined place was performed |
| Disabled | Login by user other than predetermined user was performed |
| Enabled | Mobile terminals equal to or more than preset number are present within predetermined range |

FIG. 4

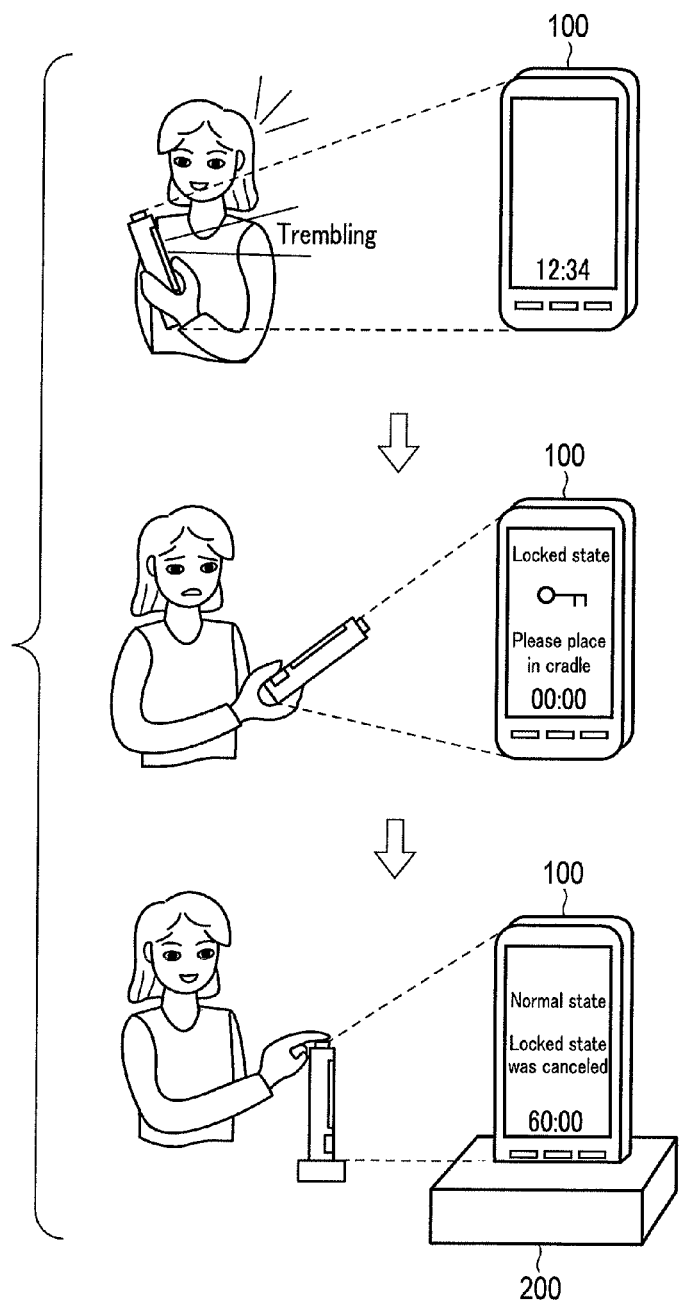
F I G. 5

MOBILE TERMINAL DEVICE, INFORMATION MANAGEMENT DEVICE, AND INFORMATION MANAGEMENT SYSTEM

CROSS-REFERENCE TO RELATED APPLICATIONS

This application is a Continuation Application of PCT Application No. PCT/JP2015/072537, filed Aug. 7, 2015 and based upon and claiming the benefit of priority from Japanese Patent Application No. 2015-010506, filed Jan. 22, 2015, the entire contents of all of which are incorporated herein by reference.

BACKGROUND OF THE INVENTION

1. Field of the Invention

The present invention relates to a mobile terminal device, an information management device, and an information management system.

2. Description of the Related Art

In recent years, with development of a technology of voice recognition, cases where some of various information communication systems effectively utilize voice recording devices are increasing. For example, in medical institutions such as hospitals, an information management system or the like that manages information of a medical chart (medical examination record information) of each patient has been put to practical use.

The information management system includes a server that stores the medical examination record information and a terminal device that is connected with the server through a network, reads out the medical examination record information from the server, and displays it.

For example, the terminal device includes an operation input section, a sound recording section, an information input section such as an imaging section. The terminal device can add information input through the information input section to the medical examination record information on the server. For example, Jpn. Pat. Appln. KOKAI Publication No. 2006-31517 discloses an intra-hospital action analysis system that monitors and analyzes actions of medical workers in a hospital so that the medical examination record information and the like cannot be rewritten in such a system.

Information of a human voice like the medical examination record information is personal information that requires high security. In particular, when a network concerns, strict management is required.

It is an object of the present invention to provide a mobile terminal device, an information management device, and an information management system having higher security.

BRIEF SUMMARY OF THE INVENTION

According to the present invention, it is possible to provide the mobile terminal device, the information management device, and the information management system having the higher security.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a view for explaining a structural example of an information management system according to an embodiment;

FIG. 2 is a view for explaining a structural example of a mobile terminal device according to an embodiment;

FIG. 3 is a view for explaining a structural example of an information management device according to an embodiment;

FIG. 4 is a view for explaining an example of locking conditions according to an embodiment;

FIG. 5 is a view for explaining an example of an operation of the mobile terminal device according to an embodiment;

DETAILED DESCRIPTION OF THE INVENTION

Figure 6:
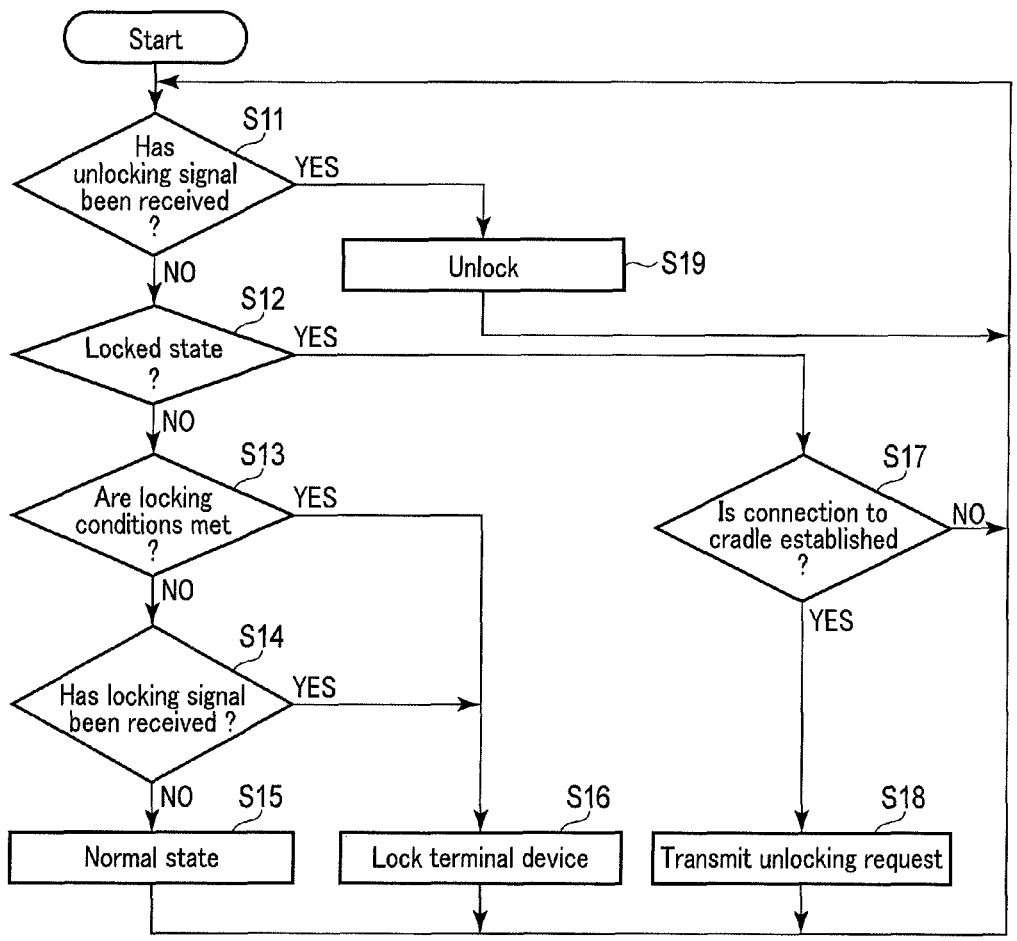
FIG. 6 is a view for explaining an example of an operation of the mobile terminal device according to an embodiment.

A mobile terminal device, an information management device, and an information management system according to an embodiment will now be described hereinafter with reference to the drawings.

FIG. 1 shows a structural example of an information management system 1.

FIG. 1 shows an example of a system constituted of electronic devices. The information management system 1 has, e.g., a mobile terminal device 100, a cradle 200, an information management device 300, and others.

Here, a description will be given on the assumption of use in a medical institution or the like. For example, when a mobile terminal is taken out of a medical institution in a state that a medical examination record information is held, there is a possibility that the medical examination record information leaks, and the prevention can be a very serious problem. The mobile terminal device 100 is an electronic device that performs access to a network, input of information, display of information, and others in response to an operation.

The mobile terminal device 100 is, e.g., a mobile phone terminal, a tablet type PC, or any other electronic device.

The cradle 200 is an electronic device that performs supply of power to the mobile terminal device 100, relay of communication using the mobile terminal device 100, and others.

The information management device 300 is an electronic device that manages information. Further, the information management device 300 is a host device that communicates with the mobile terminal device 100 and controls locking of the mobile terminal device 100. When the information management system 1 is used in a medical institution, the information management device 300 records information of a medical chart (medical examination record information) of each patient and others. Furthermore, the information management device 300 carries out output and update of the medical examination record information as required. The information management device 300 is an electronic device such as a PC or a server.

The mobile terminal device 100 is connected to the information management device 300 through a network 400. In the example of FIG. 1, access points 500A and 500B are connected to the network 400. Moreover, the information management device 300 is wire-connected to the network 400. The access point 500A and the access point 500B are access points installed at different sites. It is to be noted that, when the access point 500A and the access point 500B do not have to be discriminated from each other, each of them is called an access point 500.

The access point 500 is an access point that connects an electronic device corresponding to wireless communication with the network 400. It is to be noted that the access point 500 may have a function of a router, or a router may be separately provided. Additionally, the access point 500 may be configured to function as a hub that connects an electronic device with the network through a cable.

The access point 500 can perform the wireless communication with, e.g., the mobile terminal device 100. That is, the mobile terminal device 100 can be connected to the network 400 through the access point 500.

Further, the cradle 200 may be connected to the access point 500. The cradle 200 includes a slot in which the mobile terminal device 10 can be disposed. Furthermore, the cradle 200 includes a contact terminal that enables communication with the mobile terminal device 10 when the mobile terminal device 100 is disposed in the slot. Consequently, when the mobile terminal device 100 is mounted in the cradle 200, it can perform wire communication with the access point 500 through the cradle 200 when it is mounted in the cradle 200. That is, the mobile terminal device 100 can be connected to the network 400 through the cradle 200 and the access point 500.

It is to be noted that the mobile terminal 100 is connected to the access point 500 through a communication protocol that enables bidirectional communication. For example, the mobile terminal device 100 and the access point 500 can perform the wireless communication with each other through a communication protocol such as IEEE802.11, Wi-Fi (a registered trademark), or Bluetooth (a registered trademark).

With the above-described configuration, the mobile terminal device 100 can communicate with the information management device 300. It is to be noted that the mobile terminal device 100 has means for establishing a connection with the access point 500 by the wireless connection and means for establishing a connection with the access point 500 by the wire connection. Consequently, when the mobile terminal device 100 is mounted in the cradle 200 or when it is present in a communicable range of the access point 500, the mobile terminal device 100 can execute browsing, addition of a postscript, update, and others of the medical examination record information recorded by the information management device 300.

Furthermore, the mobile terminal device 100 stores preset locking conditions. The locking conditions are determined by the information management device 300. The mobile terminal device 100 stores the locking conditions transmitted from the information management device 300. Moreover, the mobile terminal device 100 sequentially confirms a state of itself. Consequently, whether the locking conditions are met is determined. When the mobile terminal device 100 determines that the locking conditions are met, it switches itself from a normal state to a locked state. When the mobile terminal device 100 is in the locked state, various functions are limited. For example, when the mobile terminal device 100 is in the locked state, it does not accept operations.

That is, when the mobile terminal device 100 is in the locked state, it limits browsing, addition of a postscript, update, and others of the medical examination record information. Consequently, an erroneous operation when a situation is not normal or an intentional operation by a malicious third person can be prevented, and an unintended or intended information leak and others can be avoided. If such effects can be exerted, other limits may be adopted, and ingenuity may be exercised to discourage from performing such actions by giving a warning or allowing a motion different from a normal state.

For example, the access point 500 and the cradle 200 connected to the access point are installed in a medical institution alone. Under such a situation, in a case where the locking conditions of the mobile terminal device 100 are set so that the device itself is locked if the device is not connected to the cradle 200 for a fixed time, it is possible to prevent the mobile terminal device 100 from being operated for a fixed time or more outside the medical institution. In this manner, the mobile terminal device 100 can improve security of information held by itself by locking itself (including a warning and the like other than limitation of functions) when it is not connected to the cradle 200 for a fixed time or more.

Further, the mobile terminal device 100 determine its own position based on the access point 500A or 500B or the like for use in communication or based on a function such as GPS. For example, in a case where the locking conditions of the mobile terminal device 100 are set so that the mobile terminal device 100 itself is locked when it is used somewhere other than a predetermined position, the mobile terminal device 100 can be prevented from being operated somewhere other than the predetermined position. The mobile terminal device 100 can improve security of information by locking itself when it is used somewhere other than the predetermined position. Furthermore, it is possible to prevent unforeseen circumstances or avoid deliberate fraudulent operations.

When the mobile terminal device 100 is connected with the cradle 200, an unlocking request is transmitted to the information management device 300. When the information management device 300 has received the unlocking request, it determines whether unlocking the mobile terminal device 100 is appropriate, and transmits an unlocking signal to the mobile terminal device 100 if unlocking is determined to be appropriate. When the mobile terminal device 100 has received the unlocking signal, it unlocks itself. Consequently, limited functions can be resumed, or irregular operations are stopped.

FIG. 2 shows a structural example of the mobile terminal device 100 and the cradle 200.

The mobile terminal device 100 includes a control section 101, a display section 102, a sound output section 103, an imaging section 104, a sound recording section 105, an operation input section 106, a clock section 107, a position detecting section 108, a function limiting section 109, a memory section 110, a wireless communicating section 111, a wire communicating section 112, and a power supply section 113.

The control section 101 controls operations of the respective sections in the mobile terminal device 100. The control section 101 includes a CPU, an ROM, a RAM, a nonvolatile memory, and others.

The CPU is an arithmetic operation element that can execute various kinds of arithmetic processing. The CPU realizes various functions by executing a program stored in the ROM, the nonvolatile memory, or the like. The ROM stores, e.g., a program configured to control the mobile terminal device 100 or a program configured to realize various kinds of functions. The RAM functions as a work memory of the CPU. That is, the RAM stores arithmetic results of the CPU, data read by the CPU, and others. The nonvolatile memory is a nonvolatile memory that stores various kinds of setting information, a program, and others.

The CPU starts a program stored in the ROM or the nonvolatile memory based on an operation signal supplied from the operation input section 106. Consequently, the control section 101 can control operations of the respective sections in the mobile terminal device 100. Furthermore, the control section 101 may include an image processing function of generating a video signal that is displayed in a display apparatus of the display section 102.

The display section 102 includes, e.g., the display apparatus and a drive circuit that displays various screens in the display apparatus based on control of the control section 101. The display apparatus of the display section 102 includes, e.g., a liquid crystal display panel including pixels aligned in a matrix form and a backlight that illuminates this liquid crystal panel. Moreover, the display apparatus of the display section 102 may be configured to include an organic EL display in which organic EL elements are aligned in a matrix form. The display section 102 displays video in the display apparatus based on a video signal supplied from the control section 101.

The sound output section 103 is an audio output apparatus (e.g., a speaker) that outputs sound. For example, the sound output section 103 can reproduce and output sound data recorded by the mobile terminal device 100.

The imaging section 104 includes a lens, an imaging element, and an analog/digital converter (ADC). The lens forms an image of light transmitted therethrough on the imaging element. The imaging element includes a pixel array in which pixels that photo-electrically convert a subject image transmitted through the lens are two-dimensionally aligned. The ADC quantizes electric charges generated by the imaging element.

Each pixel in the imaging element can store photo-electrically convert the light transmitted through the lens and store an electric charge. The imaging element is, e.g., a Charge-Coupled Device (CCD), a Complementary Metal Oxide Semiconductor (CMOS), or any other two-dimensional imaging element.

The lens is an optical system formed of a combination of lenses. The optical system includes, e.g., a focusing lens, a zooming lens, a diaphragm blade, and others. The lens drives the focusing lens in the optical system and forms a subject image on the imaging element based on control of the control section 101.

Moreover, the imaging section 104 reads out the electric charge stored in the imaging element as a signal, executes signal processing (e.g., analog amplification) to the read signal, and outputs the signal subjected to the signal processing to the ADC. The ADC quantizes a signal supplied from the signal processing section, and acquires image data. Consequently, the imaging section 104 can acquire image data.

Additionally, the imaging section 104 may be configured to include a mount to which an interchangeable lens can be mounted in place of the lens.

The sound recording section 105 incudes a stereo microphone configured to acquire sound. The sound recording section 105 can acquire stereo sound (sound data) by using the stereo microphone. Further, the sound recording section 105 can acquire monaural sound data by using the stereo microphone. The control section 101 generates a time stamp by using the clock section 107, and adds the time stamp to the acquired sound data.

The operation input section 106 includes an operation key through which an operation signal is generated in accordance with input of an operation performed by a user, a touch sensor, and others. Furthermore, the operation input section 106 may be configured to receive the operation signal from a keyboard, a mouse, or any other input apparatus that can generate the operation signal. The operation input section 106 supplies the operation signal to the control section 101. It is to be noted that the touch sensor includes a capacitive sensor or a device that generates positional information based on any other system.

The clock section 107 is a module that measures the time. It is to be noted that the clock section 107 can measure a current time by measuring an elapsed time from a preset time. The clock section 107 can output the current time as a time stamp. Further, the clock section 107 can measure an elapsed time from disconnection from the cradle 200 or an elapsed time from end of a charging state. The clock section 107 supplies the current time, the elapsed time from disconnection from the cradle 200, the elapsed time from end of the charging state, or the like as time information to the control section 101 or the function limiting section 109. Furthermore, when connection with the cradle 200 is again established after disconnection from the cradle 200, or when charging is again started after end of the charging state, the clock section 107 may reset an elapsed time that has been measured. It is to be noted that the clock section 107 may be configured to include a function of a radio clock.

The position detecting section 108 has a function of detecting its own position. The position detecting section 108 can generate positional information indicative of a current position of the mobile terminal device 100 based on a signal output from, e.g., a GPS satellite or the like. Moreover, the access points 500A and 500B and any other access point include identifiers different from each other (e.g., MAC addresses). The position detecting section 108 may be configured to generate the positional information by recognizing an identifier of an access point to which access is gained. For example, the mobile terminal device 100 previously stores a table in which the positional information is associated with the identifiers of the respective access points. The position detecting section 108 can recognize the positional information by extracting the positional information associated with the identifier of the access point to which access is gained from the table. The position detecting section 108 basically supplies positional information when this device is used to the control section 101 or the function limiting section 109.

Additionally, the positional information may be configured to have information indicative of a position provided at every predetermined time. That is, the positional information may be configured to have information indicative of a history of current positons of the mobile terminal device 100 provided at every predetermined time. When the positional information has such a configuration, the function limiting section 109 can identify a moving path of an operator having the mobile terminal device 100 based on the positional information. When such an action history itself or a future action that can be predicted from the action history is far from a regular one and can be considered to be suspicious, a measure such as locking described above can be taken to prevent unauthorized use, leak, or acquisition of information. As information worth protecting (information to be guarded), both information accessed by this device and information recorded in this device are assumed (information guard).

The function limiting section 109 determines whether a state of the mobile terminal device 100 meets the preset locking conditions. The locking conditions are, e.g., a list of states of the mobile terminal device 100. The locking conditions are stored by the memory section 110. The function limiting section 109 may be configured to include a memory that stores the locking conditions transmitted from the information management device 300. Consequently, the locking conditions can be set in a communication environment in advance, and locking and the like can be performed even outside the communication environment. Further, when an action is predicted and the conditions are met by prediction, the rapid information guard can be carried out. Furthermore, for example, the nonvolatile memory or the RAM of the control section 101 may be configured to store the locking conditions.

When the function limiting section 109 determines that the locking conditions are met, it locks the mobile terminal device 100. As information indicative of a state of the mobile terminal device 100 (state information), the function limiting section 109 uses the time information, the positional information, or any other information. That is, the state information is compared information for use in a determination on whether the locking conditions are met.

The function limiting section 109 determines whether the preset locking conditions are met based on a state of the mobile terminal device 100 indicated by the state information. When the preset locking conditions are net, the function limiting section 109 disables the imaging section 104, the sound recording section 105, the operation input section 106, and others. That is, the mobile terminal device 100 enters a state that it accepts no operation input in the locked state. Additionally, the mobile terminal device 100 may be configured to accept some predetermined operations alone in the locked state. At the risk of repetition, functions other than the normal functions, e.g., a warning, a siren, or procurement of evidences by starting sound recording may be actuated.

Further, in a case where the medical examination record information is stored in the memory section 110, the RAM of the control section 101, the nonvolatile memory of the control section 101, or the like when the mobile terminal device 100 is locked, the function limiting section 109 may be configured to delete the stored medical examination record information. Consequently, the mobile terminal device 100 can limit browsing, addition of a postscript, update, and others of the medical examination record information and perform the information guard in the locked state.

Furthermore, in a case where the medical examination record information is stored in the memory section 110, the RAM of the control section 101, the nonvolatile memory of the control section 101, or the like when the mobile terminal device 100 is locked, the function limiting section 109 may be configured to delete the stored medical examination record information. Consequently, the mobile terminal device 100 can limit browsing, addition of a postscript, update, and others of the medical examination record information in the locked state.

Moreover, when the function limit section 109 is connected with the cradle 200, it transmits an unlocking request to the information management device 300. In this case, the function limiting section 109 functions as an unlocking request section.

Additionally, when the function limiting section 109 has received an unlocking signal from the information management device 300, it cancels the locked state. It is to be noted that data transmitted from the information management device 300 can be analyzed and thereby recognized by the control section 101. The control section 101 controls the function limiting section 109 to cancel the locked state when the received data is the unlocking signal. Consequently, when a user just tries charging without consciousness, the mobile terminal device 100 is switched from the locked state to the normal state without any special action.

The memory section 110 is a memory that stores information. The memory section 110 includes a storage medium such as a hard disk drive (HDD), a solid state drive (SSD), or a semiconductor memory. Further, the memory section 110 may be configured to include a memory I/F or the like that can be connected to a storage medium such as a memory card in place of including the storage medium. The memory section 110 can store information in the storage medium based on the control of the control section 101. The control section 101 stores the locking conditions received from the information management device 300 in the memory section 110.

The wireless communicating section 111 is an interface for use in communication with the access point 500 in the wireless communication. The wireless communicating section 111 can communicate with any other device connected to the network 400 through the access point 500.

Further, the wireless communicating section 111 can detect other mobile terminal devices 100 present in the communicable range. For example, the wireless communicating section 111 can recognize the number of other mobile terminal devices 100 present in the communicable range by detecting changes in electric waves.

In such an environment, it is possible to perform not only a stand-alone type state determination but also information management by monitoring a relationship between devices, thereby enabling an advanced determination or measure. The wireless communicating section 111 supplies information indicative of the number of other mobile terminal devices 100 present in the communicable range (number information) as state information to the control section 101 or the function limiting section 109.

The wire communicating section 112 is an interface for use in communication with other devices connected to the network 400 by the wire communication. The wire communicating section 112 includes a contact terminal connected to a contact terminal provided in the slot of the cradle 200 when the mobile terminal device 100 is mounted in the slot of the cradle 200. That is, when the mobile terminal device 100 is mounted in the slot of the cradle 200, the mobile terminal device 100 is electrically connected to the cradle 200. Consequently, the mobile terminal device 100 can perform the wire communication with the access point 500 through the cradle 200 when it is mounted in the cradle 200.

That is, the mobile terminal device 100 can be connected to the network 40 through the cradle 200 and the access point 500.

That is, the wireless communicating section 111 and the wire communicating section 112 function as communicating sections that communicate with the information management device 300 which is a host device. Furthermore, the wire communicating section 112 detects establishment of connection with the cradle 200 that supplies electric power to the mobile terminal device 100. Moreover, the function limiting section 109 transmits the unlocking request to the information management device 300 which is the host device when the wire communicating section 112 detects that the connection with the cradle 200 has been established.

The power supply section 113 includes a battery and a DC jack that is connected to an adapter that receives electric power from a commercial power source or the like. Additionally, the power supply section 113 may be configured to receive the electric power from the cradle 200 when the mobile terminal device 100 is connected to the cradle 200 through the contact terminal of the wire communicating section 112. In this case, two of terminals of the connection terminal that connects the mobile terminal device 100 to the cradle 200 are constituted as power supply terminals. The power supply section 113 changes the battery with the received electric power. Further, the power supply section 113 can supply the electric power that has charged the battery to the respective sections in the mobile terminal device 100. This cradle has the charging function and the communicating function, but the charging function is not required. Furthermore, it may cooperate with a PC or the like, or may cooperate with a biometric system that can acquire fingerprints, voiceprints, and facial information.

The control section 101 can request the information management device 300 for the medical examination record information based on an operation signal supplied from the operation input section 106. For example, the control section 101 transmits a request (the medical examination record information) including a patient ID or the like as identifying information assigned to each patient to the information management device 300. Consequently, the control section 101 can receive the medical examination record information associated with the transmitted patient ID on the information management device 300. Moreover, the control section 101 can store the medical examination record information received from the information management device 300 in the memory section 110 or the nonvolatile memory or the like in the control section 101. That is, the control section 101 functions as an information acquiring section that acquires the medical examination record information stored in the information management device 300.

Additionally, the control section 101 can display the stored medical examination record information in the display apparatus of the display section 102. Consequently, the mobile terminal device 100 allows an operator of the mobile terminal device 100 to browse the medical examination record information.

Further, the control section 101 can generate additional information for use in addition of information to the medical examination record information based on an operation signal generated by the operation input section 106, an image generated by the imaging section 104, or sound data generated by the sound recording section 105.

Furthermore, the control section 101 can upload the generated additional information to the information management device 300. It is to be noted that, in this case, the control section 101 likewise associates the additional information with a patient ID of each patient and uploads it to the information management device 300. Consequently, the mobile terminal device 100 can add a postscript to or update the medical examination record information stored in the information management device 300. That is, the control section 101 functions as an information adding section that generates additional information in accordance with input of an operation, uploads the generated additional information to the information management device 300, and adds it to the medical examination record information.

It is to be noted that the mobile terminal device 100 may be configured to enable browsing, addition, and update of the medical examination record information when login to the information management device 300 has succeeded. Thus, the control section 101 generates a login ID and a PIN in accordance with an operation signal, and transmits the generated login ID and PIN to the information management device 300. The information management device 300 determines whether the received login ID and PIN are correct, and accepts browsing, addition, and update of the medical examination record information when the received login ID and PIN are determined to be correct. These steps may be omitted in accordance with a system.

Moreover, the control section 101 may be configured to count the number of times of login and the number of login errors per login ID. In this case, the control section 101 adds information indicative of the number of times of login and the number of login errors per login ID (login information) to the state information.

As described above, the control section 101 treats the time information generated by the clock section 107, the positional information generated by the position detecting section 108, the login information, the number information, and others as the state information. That is, the control section 101, the clock section 107, the position detecting section 108, and the wireless communicating section 111 can be referred to as state determining sections that determine a state of the mobile terminal device 100 and generate the state information. For example, the control section 101 holds the state information in the RAM, the nonvolatile memory, the memory section 110, or the like.

The cradle 200 includes a control section 201, a wire communicating section 202, and a power supply section 203.

The control section 201 controls operations of the respective sections in the cradle 200. For example, the control section 201 detects whether the mobile terminal device 100 is connected to the wire communicating section 202. The control section 201 communicates with the mobile terminal device 100 through the wire communicating section 202 when the mobile terminal device 100 is connected to the wire communicating section 202.

The wire communicating section 202 functions as an interface that establishes the wire communication with the access point 500. The wire communicating section 202 is connected to the connection terminal of the access point 500 through, e.g., an LAN cable. Additionally, the wire communicating section 202 also functions as an interface that establishes the communication with the mobile terminal device 100. The wire communicating section 202 includes a contact terminal in the slot of the cradle 200. When the mobile terminal device 100 is mounted in the slot of the cradle 200, this contact terminal is connected with the contact terminal of the wire communicating section 112 of the mobile terminal device 100, and the mobile terminal device 100 is electrically connected to the cradle 200.

The power supply section 203 includes a DC jack that is connected to an adapter that receives electric power from a commercial power source or the like. The power supply section 203 supplies the received electric power to the mobile terminal device 100 connected through the wire communicating section 202. For example, the power supply section 203 uses two of terminals of the contact terminal of the wire communicating section 202 to supply the electric power to the mobile terminal device 100.

It is to be noted that the control section 201 of the cradle 200 may include an ROM or a nonvolatile memory storing identifying information such as an MAC address of a unique ID. Further, for example, the ROM or the nonvolatile memory of the control section 101 in the mobile terminal device 100 may be configured to previously store identifying information of the paired cradle 200. In this case, the control section 101 reads out the identifying information of the connected cradle 200, and compares it with the identifying information stored in the ROM or the nonvolatile memory of the control section 101. When a result of comparison is a match, the control section 101 determines that the connected cradle 200 is the previously paired cradle 200. When the connected cradle 200 is determined to be the previously paired cradle 200, the control section 101 starts charging using the power supply section 113. Furthermore, when the connected cradle 200 is determined to be the previously paired cradle 200, the control section 101 controls the function limiting section 109 to transmit the unlocking request to the information management device 300.

FIG. 3 shows a structural example of the information management device 300.

The information management device 300 includes a control section 301, a display section 302, an operation input section 303, a memory section 304, a communicating section 305, a power supply section 306, a state identifying section 308, a locking condition setting section 309, a locking section 310, an unlocking section 311, and a textizing section 312.

The control section 301 controls operations of the respective sections in the information management device 300. The control section 301 includes a CPU, an ROM, an RAM, a nonvolatile memory, and others.

The CPU starts a program stored in the ROM or the nonvolatile memory based on an operation signal supplied from the operation input section 303 or various kinds of signals received through the communicating section. Consequently, the control section 301 can control operations of the respective sections in the information management device 300. Further, the control section 301 may include an image processing function of generating a video signal that is displayed in a display apparatus of the display section 302.

The display section 302 includes, e.g., the display apparatus and a drive circuit that displays various screens in the display apparatus based on control of the control section 301. The display apparatus of the display section 302 includes, e.g., a liquid crystal display panel including pixels aligned in a matrix form and a backlight that illuminates this liquid crystal panel. Moreover, the display apparatus of the display section 302 may be configured to include an organic EL display in which organic EL elements are aligned in a matrix form. The display section 302 displays video in the display apparatus based on a video signal supplied from the control section 301.

The operation input section 303 includes an operation key through which an operation signal is generated in accordance with input of an operation performed by a user, a touch sensor, and others. Furthermore, the operation input section 303 may be configured to receive the operation signal from a keyboard, a mouse, or any other input apparatus that can generate the operation signal. The operation input section 303 supplies the operation signal to the control section 301. It is to be noted that the touch sensor includes a capacitive sensor or a device that generates positional information based on any other system.

The memory section 304 is a memory that stores information. The memory section 304 includes a storage medium such as a hard disk drive (HDD), a solid state drive (SSD), or a semiconductor memory. Further, the memory section 304 may be configured to include a memory I/F or the like that can be connected to a storage medium such as a memory card in place of including the storage medium. The memory section 304 can store information in the storage medium based on the control of the control section 301. It is to be noted that, for example, a patient ID is assigned to each patient and the memory section 304 stores the medical examination record information in accordance with each patient ID.

Consequently, a database from which the medical examination record information can be called up from each patient ID is configured in the memory section 304.

Furthermore, the memory section 304 stores locking conditions in accordance with each mobile terminal device 100. For example, the memory section 304 stores identifying information such as an MAC address of each mobile terminal device 100 in association with the locking conditions.

The communicating section 305 is an interface that establishes communication with other devices connected to the network 400 by the wire connection. The communicating section 305 includes a terminal that can be connected with, e.g., an LAN cable. It is to be noted that the communicating section 305 may be configured to be connected to the network 400 by the wireless connection.

The power supply section 306 receives electric power from a commercial power source or the like, converts a voltage, and supplies it to the respective sections in the information management device 300.

The state identifying section 308 is a module that identifies a state of the mobile terminal device 100 connected to the network 400. In case of communicating with the information management device 300, the mobile terminal device 100 transmits information indicative of various kinds of states to the information management device 300. For example, the mobile terminal device 100 transmits state information, information indicating whether a locked state is provided, and others to the information management device 300. The state identifying section 308 identifies whether the mobile terminal device 100 is in the locked state based on, e.g., the information indicating whether the locked state is provided transmitted from the mobile terminal device 100. Moreover, the state identifying section 308 recognizes time information, positional information, and others of the mobile terminal device 100 based on the state information.

The locking condition setting section 309 sets locking conditions for each mobile terminal device 100 in accordance with an operation signal. There are such locking conditions as shown in FIG. 4. This shows the operation input section that accepts operations as well as contents of the memory section that previously stores a list of states when the mobile terminal device is sued as the locking conditions to determine a state at the time of limiting operations of the mobile terminal device. These are an example to estimate a situation where a device user has a malicious intent when his/her behavior is irregular or an unintended user does not use the device in a normal manner, and various exceptional measures or options may be provided in accordance with an environment for use of various devices or systems.

According to the example shown in FIG. 4, the locking conditions are conditions such as "connection to a cradle was not established for a predetermined time", "charging was not performed for a predetermined time", "traveling in a route other than a predetermined route was performed", "use in a place other than a predetermined place was performed", "login by a user other than a predetermined user was performed", or "mobile terminals equal to or more than a preset number are present within a predetermined range". The locking condition setting section 309 can switch enabled and disabled states of these conditions in accordance with an operation signal. Moreover, the locking condition setting section 309 allows, e.g., a system manager to add or delete new locking conditions in accordance with an operation signal.

It is to be noted that the locking conditions are generated in accordance with each mobile terminal device 100, and stored in, e.g., the memory section 304. The locking condition setting section 309 can read out corresponding locking conditions from the memory section 304 in accordance with identifying information of the mobile terminal device 100 as a communication target. Additionally, the locking condition setting section 309 transmits the locking conditions to the corresponding mobile terminal device 100. The mobile terminal device 100 stores the received locking conditions. That is, the locking condition setting section 309 functions as a locking condition transmitting section that transmits preset locking conditions to the mobile terminal device 100 by an operation.

Further, whether the locking conditions are met may be determined by the information management device 300 in place of the mobile terminal device 100. In this case, the control section 301 determines whether a state of the mobile terminal device 100 meets the locking conditions based on state information received from the mobile terminal device 100.

The locking section 310 transmits a locking signal to the mobile terminal device 100. The locking signal is a signal to forcedly set the mobile terminal device 100 to the locked state. When the mobile terminal device 100 has received the locking signal, it changes itself to the locked state. When a state of the mobile terminal 100 is determined to meet the locking conditions, the locking section 310 transmits the locking signal to the mobile terminal device 100.

The unlocking section 311 transmits an unlocking signal to the mobile terminal device 100. The unlocking signal is a signal to restore the mobile terminal device 100 to the normal state from the locked state. When the mobile terminal device 100 has received the unlocking signal, it sets itself to the normal state from the locked state. In a case where the unlocking section 311 has received an unlocking request transmitted from the mobile terminal device 100, it determines whether unlocking the mobile terminal device 100 is appropriate, and transmits the unlocking signal to the mobile terminal device 100 when unlocking is determined to be appropriate. That is, the unlocking section 311 functions as an unlocking signal transmitting section that transmits the unlocking signal to cancel the locked state of the mobile terminal device 100 to the mobile terminal device 100 when it has received the unlocking request transmitted from the mobile terminal device 100.

The textizing section 312 recognize sound and generates text data. For example, when sound data is included in received additional information, the textizing section 312 recognizes sound of utterance in the sound data, and generates the text data. The control section 301 can treat the text data generated by the textizing section 312 as the additional information. That is, the control section 301 can add the text data generated by the textizing section 312 to the medical examination record information.

When a medical examination record information request has been received from the mobile terminal device 100, the control section 301 reads out the medical examination record information requested by the mobile terminal device 100 from the memory section 304, and transmits it to the mobile terminal device 100. For example, when the control section 301 has received the medical examination record information request including a patient ID of each patient, it reads out the medical examination record information associated with the received patient ID from the memory section 304, and transmits the read medical examination record information to the mobile terminal device 100. Consequently, the information management device 300 enables an operator of the mobile terminal device 100 to browse the requested medical examination record information.

Furthermore, the control section 301 can add or update information of the medical examination record information based on the additional information transmitted from the mobile terminal device 100. For example, the control section 301 identifies the medical examination record information to which the additional information is added based on the patient ID of each patient associated with the additional information. Moreover, the control section 301 adds the additional information to the identified medical examination record information. Consequently, the information management device 300 can add a postscript to or update the medical examination record information.

Additionally, the control section 301 may be configured to authenticate the mobile terminal device 100 and allow browsing, addition, update, and the like of the medical examination record information when a login ID and a PIN transmitted from the mobile terminal device 100 are correct. In this case, the control section 301 stores combinations of login IDs and PINs in the memory section 304 or the like in advance. When a login ID and a PIN coinciding with the login ID and the PIN transmitted from the mobile terminal device 100 are stored, the control section 301 authenticates the mobile terminal device 100. When the information management device 300 has authenticated the mobile terminal device 100, it accepts browsing, addition, and update of the medical examination record information.

FIG. 5 shows an example of an operation of the mobile terminal device 100. It is to be noted that, here, a description will be given as to an example where "connection to a cradle was not established for a predetermined time" is set to the mobile terminal device 100 as a locking condition. In this case, the control section 101 of the mobile terminal device 100 counts an elapsed time from disconnection from the cradle 200 by using the clock section 107. When this elapsed time has reached a predetermined time decided by the locking condition, the control section 101 sets the mobile terminal device 100 to the locked state by using the function limiting section 109.

First, when the mobile terminal device 100 is in the normal state, the control section 101 allows the display section 102 to display a time required until the mobile terminal device 100 is locked. The control section 101 calculates the time required until the mobile terminal device 100 is locked from the predetermined time decided by the locking condition and the elapsed time from disconnection from the cradle 200, and displays it in the display section 102.

Further, the mobile terminal device 100 may be configured to vibrate a housing of the mobile terminal device 100 by a non-illustrated vibrating section when the time required until locking becomes less than a preset threshold value. Furthermore, the mobile terminal device 100 may be configured to allow the sound output section 103 to output sound, e.g., a beep when the time required until locking becomes less than the preset threshold value. Consequently, the mobile terminal device 100 can inform an operator of the mobile terminal device 100 of the time required until locking.

Then, when the elapsed time from disconnection from the cradle 200 has reached the predetermined time decided by the locking condition, the function limiting section 109 switches the mobile terminal device 100 from the normal state to the locked state. Moreover, the control section 101 displays a message indicating that the mobile terminal device 100 is locked and a message that urges the mobile terminal device 100 to be connected to the cradle 200 in the display section 102. Consequently, the control section 101 can inform the operator of the mobile terminal device 100 of the effect that the mobile terminal device 100 is locked and a procedure of unlocking.

Subsequently, when the mobile terminal device 100 in the locked state is connected to the cradle, the control section 101 transmits the unlocking request to the information management device 300. Further, upon receiving the unlocking signal from the information management device 300, the function limiting section 109 switches the mobile terminal device 100 from the locked state to the normal state. Furthermore, the control section 101 allows the display section 102 to display a message indicating that the mobile terminal device 100 is unlocked. Consequently, the control section 101 can inform the operator of the mobile terminal device 100 of the effect that the mobile terminal device 100 is unlocked.

As described above, the control section 101 of the mobile terminal device 100 generates time information indicative of the elapsed time from disconnection from the cradle 200 as the state information. The function limiting section 109 determines whether the elapsed time from disconnection from the cradle 200 has reached the predetermined time indicated by the locking condition based on the state information, and switches the mobile terminal device 100 to the locked state when the elapsed time is determined to have reached the predetermined time.

Moreover, when the locking condition "charging was not performed for a predetermined time" is set, the function limiting section 109 determines whether the mobile terminal device 100 has not been changed for a predetermined time based on the state information (e.g., the time information). When the function limiting section determines that the mobile terminal device 100 has not been changed for the predetermined time, it locks the mobile terminal device 100.

That is, the control section 101 of the mobile terminal device 100 generates the time information indicative of the elapsed time from interruption of charging as the state information. The function limiting section 109 determines whether the elapsed time from interruption of charging has reached the predetermined time indicated by the locking condition based on the state information, and switches the mobile terminal device 100 to the locked state when the elapsed time is determined to have reached the predetermined time.

Additionally, when the locking condition "traveling in a route other than a predetermined route was performed" is set, the function limiting section 109 identifies a moving path of the mobile terminal device 100 based on the state information (e.g., the positional information). The function limiting section 109 determines whether the moving path of the mobile terminal device 100 is the predetermined route. When the mobile terminal device 100 is determined to have been moved in a route which is not the predetermined route, the function limiting section 109 locks the mobile terminal device 100.

That is, the control section 101 of the mobile terminal device 100 generates information indicative of the moving path of the mobile terminal device 100 as the state information. The function limiting section 109 determines whether the moving path is the predetermined route indicated by the locking condition based on the state information, and it switches the mobile terminal device 100 to the locked state when the moving path is determined not to be the predetermined route.

Further, when the locking condition "use in a place other than a predetermined place was performed" is set, the function limiting section 109 determines whether the mobile terminal device 100 has been used in a place that is not the predetermined place based on the state information (e.g., the positional information). When the mobile terminal device 100 is determined to have been used in a place that is not the predetermined place, the function limiting section 109 locks the mobile terminal device 100.

That is, the control section 101 of the mobile terminal device 100 generates the positional information indicative of a position of the mobile terminal device 100 as the state information. The function limiting section 109 determines whether the position is the predetermined position indicated by the locking condition based on the state information, and switches the mobile terminal device 100 to the locked state when the position is determined not to be the predetermined position.

Furthermore, when the locking position "login by a user other than a predetermined user was performed" is set, the function limiting section 109 determines whether login by a user other than a predetermined user was performed based on the state information (e.g., the login information). For example, in this case, the locking condition includes information indicative of a user allowed to login (the predetermined user). The function limiting section 109 can determine whether a user other than the predetermined user has logged in based on the number of times of login per login ID indicated by the login information.

When a user who is not the predetermined user is determined to have logged in, the function limiting section 109 locks the mobile terminal device 100.

That is, the control section 101 of the mobile terminal device 100 generates information indicative of a login user of the mobile terminal device 100 as the state information. The function limiting section 109 determines whether the login user is a predetermined user indicated by the locking condition based on the state information, and switches the mobile terminal device 100 to the locked state when the user is determined not to be the predetermined user.

Further, when the locking condition "mobile terminals equal to or more than a preset number are present within a predetermined distance" is set, the function limiting section 109 determines whether the mobile terminals equal to or more than a preset number are present within the predetermined distance based on the state information (e.g., the number information). When the function limiting section 109 determines that the mobile terminals equal to or more than the preset number are present within the predetermined distance, the mobile terminal device 100 is locked.

That is, the control section 101 of the mobile terminal device 100 generates information indicative of the number of other mobile terminal devices present within the predetermined distance of the mobile terminal device 100 as the state information. The function limiting section 109 determines whether the number is equal to or more than the predetermined number indicated by the locking conditions based on the state information, and switches the mobile terminal device 100 to the locked state when the number is determined to be equal to or more than the predetermined number.

Furthermore, the locking condition may be "an operation was performed outside of predetermined hours". When the locking condition "an operation was performed outside of predetermined hours" is set, the function limiting section 109 determines whether an operation has been input outside of predetermined hours based on the state information (e.g., the time information). That is, the control section 101 of the mobile terminal device 100 generates information indicative of a time at which the operation was input as the state information. The function limiting section 109 determines whether an operation has been made outside of the predetermined hours indicated by the locking condition based on the state information, and switches the mobile terminal device 100 to the switched state when the operation is determined to have been made outside of the predetermined hours. Moreover, the "predetermined hours" in this locking condition may be set in accordance with each login ID (login user).

FIG. 6 is a flowchart showing an example of an operation of the mobile terminal device 100. The control section 101 of the mobile terminal device 100 controls the function limiting section 109 at the time of turning on the power supply to sequentially execute processing shown in a flow of FIG. 6.

The function limiting section 109 determines whether the unlocking signal has been received (a step S11).

When the unlocking signal is determined not to have been received (the step S11, NO), the function limiting section 109 determines whether the mobile terminal device 100 is in the locked state (a step S12).

When the mobile terminal device 100 is determined not to be in the locked state (the step S12, NO), the function limiting section 109 determines whether the locking conditions are met (a step S13). That is, the function limiting section 109 determines whether a state of the mobile terminal device 100 meets the locking conditions based on the locking conditions stored in advance and the state information.

When the locking conditions are determined not to be met (the step S13, NO), the function limiting section 109 determines whether the locking signal has been received (a step S14).

When the locking signal is determined not to have been received (the step S14, NO), the function limiting section 109 maintains the mobile terminal device 100 in the normal state (a step S15), and shifts to processing of the step S11. In case of the normal state, the mobile terminal device 100 can accept an operation and execute various kinds of processing in accordance with the operation.

When the locking signal is determined to have been received at the step S14 (the step S14, YES), or when the locking conditions are determined to be met at the step S13 (the step S13, YES), the function limiting section 109 locks the mobile terminal device 100 (a step S16), and shifts to the processing of the step S11. That is, when the locking conditions are determined to be met, the function limiting section 109 switches the mobile terminal device 100 from the normal state to the locked state. Moreover, when the function limiting section 109 has received the locking signal transmitted from the information management device 300, it switches the mobile terminal device 100 from the normal state to the locked state.

Additionally, when the mobile terminal device 100 is determined to be in the locked state at the step S12 (the step S12, YES), the function limiting section 109 determines whether the mobile terminal device 100 is connected to the cradle 200 (a step S17).

When the mobile terminal device 100 is determined not to be connected to the cradle 20 (the step S17, NO), the function limiting section 109 shifts to the processing of the step S11 and maintains the locked state.

When the mobile terminal device 100 is determined to be connected to the cradle 200 (the step S17, YES), the function limiting section 109 transmits the unlocking request to the information management device 300 (a step S18) and shifts to the processing of the step S11.

Further, when the unlocking signal is determined to have been received at the step S11 (the step S11, YES), the function limiting section 109 unlocks the mobile terminal device 100 (a step S19), and shifts to the processing of the step S11. That is, the function limiting section 109 switches the mobile terminal device 100 from the locked state to the normal state.

Figure 7:
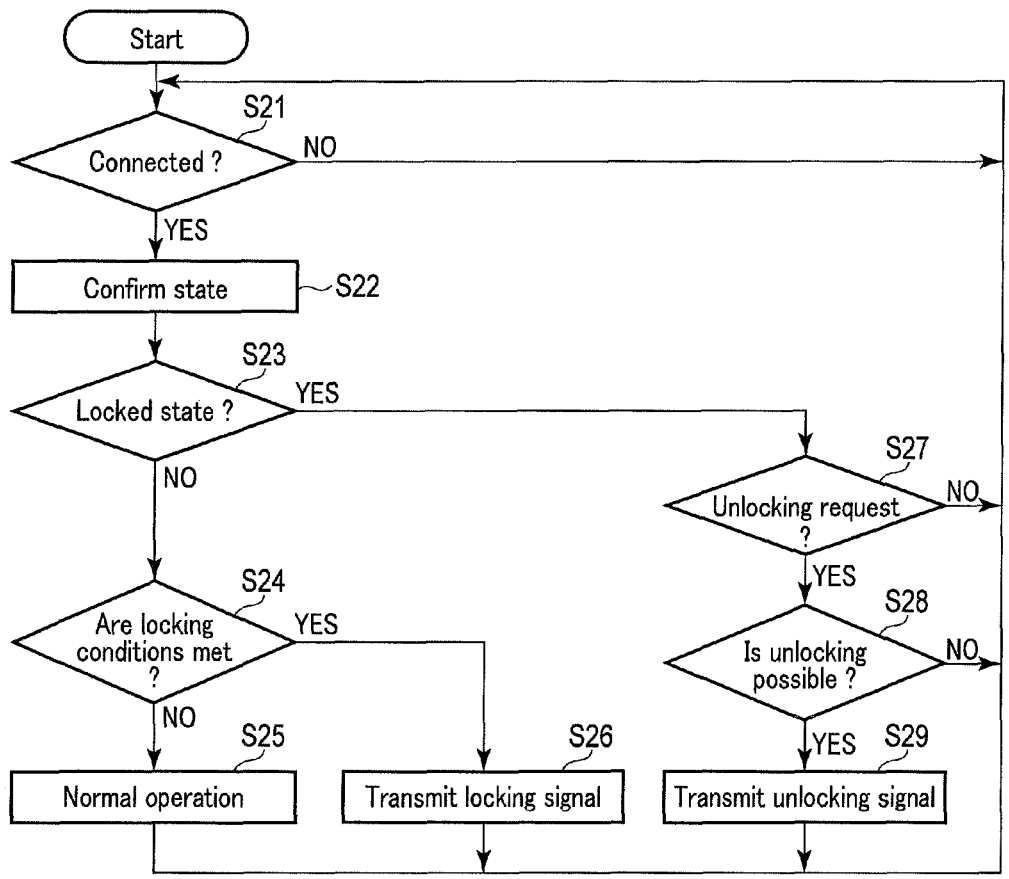
FIG. 7 is a view for explaining an example of an operation of the information management device according to an embodiment.

FIG. 7 is a flowchart showing an example of an operation of the information management device 300. The control section 301 of the information management device 300 controls the respective sections in the information management device 300 to sequentially execute processing shown in a flow of FIG. 7.

The control section 301 determines whether the mobile terminal device 100 is connected (a step S21). For example, the control section 301 determines whether the mobile terminal device 100 that has logged in the information management device 300 through the network 400 is present.

When the mobile terminal device 100 is determined to be connected (the step S21, YES), the control section 301 confirms a state of the mobile terminal device 100 by the state identifying section 308 (a step S22). That is, the control section 301 confirms the state from the mobile terminal device 100 by acquiring the state information and information indicating whether the locked state is realized or not from the mobile terminal device 100.

The control section 301 determines whether the mobile terminal device 100 is in the locked state (a step S23). That is, the control section 301 determines whether the mobile terminal device 100 is in the locked state based on the information indicating whether the locked state is realized or not acquired from the mobile terminal device 100.

When the mobile terminal device 100 is determined not to be in the locked state (the step S23, NO), the control section 301 determines whether the locking conditions are met (a step S24). That is, the control section 301 determines whether a state of the mobile terminal device 100 meets the locking conditions stored in the memory section 304. It is to be noted that the judgment on whether the locking conditions are met may be made by the mobile terminal device 100 side alone while omitting the processing of the step S24, may be made by the information management device 300 side alone while omitting the processing of the step S13 in FIG. 6, or may be made by both the mobile terminal device 100 and the information management device 300. Further, the judgments may be separately made by the mobile terminal device 100 and by the information management device 300 in accordance with contents of the locking conditions.

When the locking conditions are determined not to be met (the step S24, NO), the control section 301 performs the normal operation (a step S25). In case of performing the normal operation, the control section 301 performs output or update of the medical examination record information or other various kinds of operations in accordance with various requests from the mobile terminal device 100.

When the locking conditions are determined to be met (the step S24, YES), the control section 301 transmits the locking signal to the mobile terminal device 100 (a step S26), and shifts to processing of the operation of the step S21.

Furthermore, when the mobile terminal device 100 is determined to be in the locked state at the step S23 (the step S23, YES), the control section 301 determines whether the unlocking request has been transmitted from the mobile terminal device 100 (a step S27).

When the unlocking request is determined to have been transmitted from the mobile terminal device 100 (the step S27, YES), the control section 301 determines whether unlocking the mobile terminal device 100 is possible (a step S28). For example, the control section 301 determines whether a state of the mobile terminal device 100 does not meet the locking conditions, and decides that unlocking the mobile terminal device 100 is possible when the locking conditions are not met. It is to be noted that, when the unlocking request is determined not to have been transmitted from the mobile terminal device 10 (the step S27, NO), the control section 301 shifts to processing of the operation of the step S21.

When unlocking the mobile terminal device 100 is determined to be possible (the step S28, YES), the control section 301 transmits the unlocking signal to the mobile terminal device 100 (a step S29), and shifts to processing of the operation of the step S21. It is to be noted that, when unlocking the mobile terminal device 100 is determined to be impossible (the step S28, NO), the control section 301 shifts to processing of the operation of the step S21.

Figure 8:
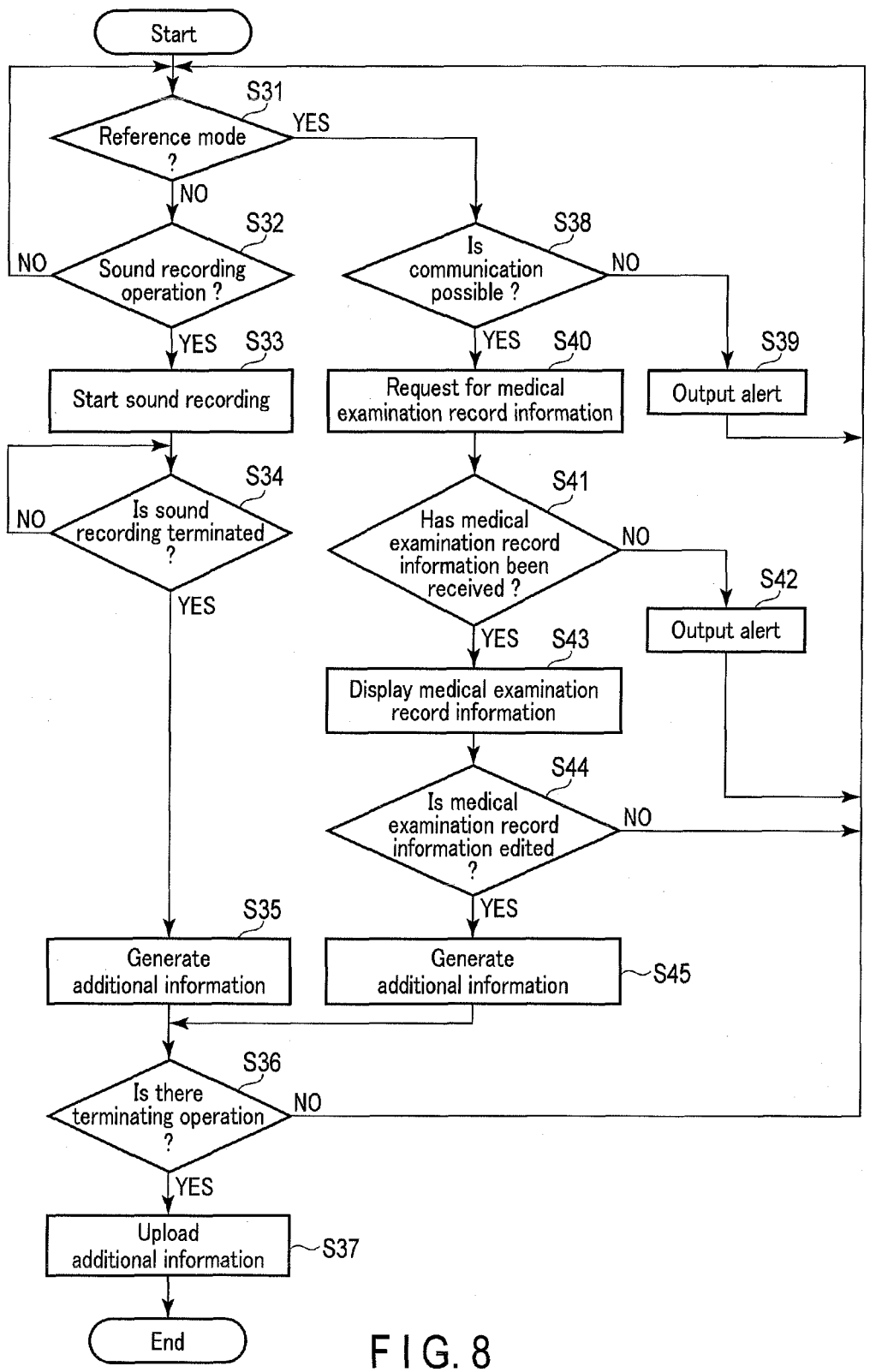
FIG. 8 is a view for explaining an example of an operation of the mobile terminal device according to an embodiment.

FIG. 8 is a flowchart showing an example of an operation in the normal state of the mobile terminal device 100. The control section 101 of the mobile terminal device 100 executes processing shown in a flow of FIG. 8 by controlling the respective sections in the mobile terminal device 100. It is to be noted that a description will be given on the assumption that the mobile terminal device 100 operates in either a reference mode to refer to the medical examination record information or a sound recording mode to add sound data to the medical examination record information, but the present invention is not restricted to this configuration. The mobile terminal device 100 may operate in an edit mode to add information to the medical examination record information or to update the medical examination record information in place of the sound recording mode. When the mobile terminal device 100 operates in the edit mode, it can treat texts generated in accordance with input of an operation, acquired image data, recorded sound data, or the like as additional information. Furthermore, the mobile terminal device 100 can edit the medical examination record information stored in the information management device 300 by uploading the additional information to the information management device 300.

As shown in FIG. 8, the control section 101 first determines whether the mobile terminal device 100 operates in the reference mode (a step S31).

When the mobile terminal device 100 is determined not to operate in the reference mode (the step S31, NO), the control section 101 decides that the mobile terminal device 100 operates in the sound recording mode, and determines whether an operation to start sound recording (a sound recording operation) has been input (a step S32). It is to be noted that, when the sound recording operation has not been input (the step S32, NO), the control section 101 shifts to processing of the step S31.

When the sound recording operation is determined to have been input (the step S32, YES), the control section 101 starts sound recording (a step S33). Moreover, the control section 101 determines whether an operation to terminate the sound recording has been input (a step S34).

When the operation to terminate the sound recording is determined to have been input (the step S34, YES), the control section 101 generates additional information (a step S35). That is, the control section 101 terminates the sound recording, and forms a file of recorded sound, and generates sound data as additional information.

The control section 101 determines whether the operation to terminate the sound recording mode has been input (a step S36). When the operation to terminate the sound recording mode is determined to have been input (the step S36, YES), the control section 101 uploads the generated additional information to the information management device 300 (a step S37), and terminates the processing. Additionally, when the operation to terminate the sound recording mode is determined not to have been input (the step S36, NO), the control section 101 shifts to processing of the step S31.

Further, when the mobile terminal device 100 is determined to operate in the reference mode at the step S31 (the step S31, YES), the control section 101 determines whether communication with the information management device 300 is possible (a step S38).

When the communication with the information management device 300 is impossible (the step S38, NO), the control section 101 outputs an alert indicating that the communication is impossible (a step S39), and shifts to processing of the step S31. For example, the control section 101 outputs an alert indicating that the access point 500 cannot be detected, that the information management device 300 cannot be found, or that the communicating function is OFF from the display section 102 or the sound output section 103.

When the communication with the information management device 300 is possible (the step S38, YES), the control section 101 requests the information management device 300 for the medical examination record information (a step S40). For example, the control section 101 creates a patient ID of each patient in accordance with input of an operation, and transmits the created patient ID to the information management device 300. Consequently, the information management device 300 can read out the medical examination record information corresponding to the received patient ID from the database, and transmit it to the mobile terminal device 100.

For example, the control section 101 may be configured to treat texts generated in accordance with input of an operation as the patient IDs. Moreover, for example, when a two-dimensional code or the like provided by coding a patient ID is printed on a patient registration card or the like, the control section 101 may be configured to read the two-dimensional code into the imaging section 104, and extract the patient ID from an image of the read two-dimensional code. Additionally, when the control section 101 has a function of extracting texts from sound, it may be configured to record the sound by using the sound recording section 105, and treat a text extracted from the recorded sound as a patient ID.

The control section 101 determines whether the medical examination record information has been received (a step S41). When the medical examination record information is determined not to have been received (the step S41, NO), the control section 101 outputs an alert (a step S42), and shifts to processing of the step S31. For example, the control section 101 outputs an alert indicating that the medical examination record information request has not been permitted or that the specified medical examination record information is not stored in the information management device from the display section 102 or the sound output section 103.

When the medical examination record information is determined to have been received (the step S41, YES), the control section 101 displays the received medical examination record information in the display section 102 (a step S43). It is to be noted that the control section 101 displays an edit button together with the medical examination record information in the display section 102. For example, when the operation input section 106 includes a touch sensor, the control section 101 displays the edit button so that it can be selected by the touch sensor. When the edit button is selected, the control section 101 displays a screen to edit the medical examination record information in the display section 102. The control section 101 generates additional information in accordance with input of an operation in this screen.

The control section 101 determines whether the medical examination record information is edited (a step S44). It is to be noted that the control section 101 may be configured to decide that the medical examination record information is edited when the edit button is selected or decide that the medical examination record information is edited in accordance with any other predetermined input operation.

When the medical examination record information is determined to be edited (the step S44, YES), the control section 101 generates additional information (a step S45), and shifts to processing of the step S36. For example, as described above, the control section 101 generates the additional information in accordance with input of an operation in a screen to edit the medical examination record information. Further, the control section 101 may be configured to generate the additional information in accordance with any other predetermined input operation. The control section 101 determines whether an operation to terminate the reference mode has been input at the step S36. When the operation to terminate the reference mode is determined to have been input, the control section 101 uploads the generated additional information to the information management device 300, and terminates the processing.

Furthermore, when the medical examination record information is determined not to be edited at the step S44 (the step S44, NO), the control section 101 shifts to processing of the step S31.

Figure 9:
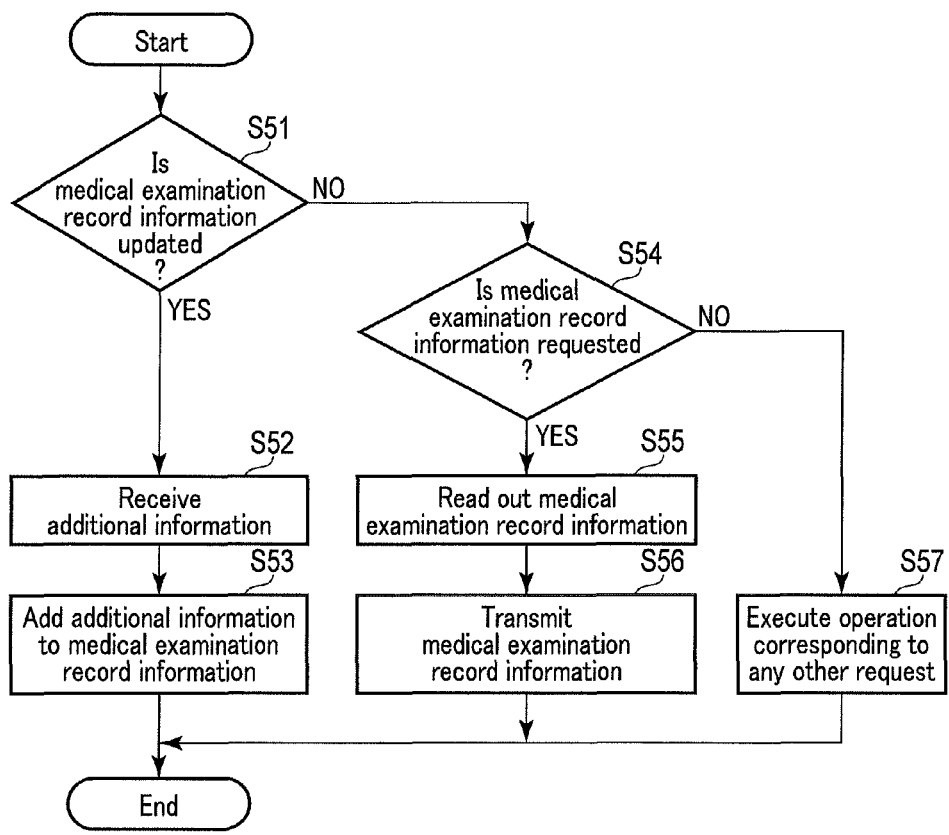
FIG. 9 is a view for explaining an operation of the information management device according to an embodiment.

FIG. 9 is a flowchart showing an example of the normal operation of the information management device 300. The control section 301 of the information management device 300 sequentially executes processing shown in a flow of FIG. 9 by controlling the respective sections in the information management device 300.

The control section 301 determines whether the medical examination result information is updated (a step S51). For example, when the additional information is uploaded from the mobile terminal device 100, the control section 301 decides to update the medical examination record information.

When the medical examination record information is determined to be updated (the step S51, YES), the control section 301 receives the additional information (a step S52). Moreover, the control section 301 adds the additional information to the medical examination record information (a step S53), and terminates the processing. It is to be noted that, in this case, the control section 301 identifies the medical examination record information to which the additional information is added based on a patient ID added to the additional information. The control section 301 adds the additional information to the identified medical examination record information. Additionally, when the received additional information is sound data, the control section 301 may be configured to extract text data from the sound data by using the textizing section 312 and add the extracted text data to the medical examination record information as additional information.

When the medical examination record information is determined not to be updated (the step S51, NO), the control section 301 determines whether the medical examination record information is requested from the mobile terminal device 100 (a step S54). That is, the control section 301 determines whether the medical examination record information request has been received from the mobile terminal device 100.

When the medical examination record information is determined to have been requested from the mobile terminal device 100 (the step S54, YES), the control section 301 reads out the medical examination record information corresponding to a patient ID included in the received medical examination record information request from the database (a step S55). Further, the control section 301 transmits the read medical examination record information to the mobile terminal device 100 (a step S56), and terminates the processing.

Furthermore, when the medical example record information is determined not to have been requested from the mobile terminal device 100 at the step S54 (the step S54, NO), the control section 301 decides that other processing different from the update of the medical examination record information and the reference of the medical examination record information is requested from the mobile terminal device 100, executes an operation corresponding to the request (a step S57), and terminates the processing.

According to the above-described configuration, when a state of the mobile terminal device 100 itself coincides with the preset locking conditions, the mobile terminal device 100 can be locked without communicating with any other device. Moreover, the mobile terminal device 100 can forcedly lock itself in accordance with the locking signal transmitted from the information management device 300. For example, when locking conditions that restrict taking out of a medical institution are set in advance, the medical examination record information can be prevented from being taken out by the mobile terminal device 100. Consequently, it is possible to provide the mobile terminal device, the information management device, and the information management system having high security.

Additionally, according to the above-described configuration, the mobile terminal device 100 can be unlocked only when the unlocking signal transmitted from the information management device 300 is received. Consequently, switching of the mobile terminal device 100 from the locked state to the normal state can be intensively managed on the information management device 300 side.

It is to be noted that the mobile terminal device 100 may be configured to unlock itself when it is detected that the mobile terminal device 100 is connected to the cradle 200 rather than unlocking itself upon receiving the unlocking signal. According to this configuration, since the mobile terminal device 100 can be readily unlocked, usability can be improved. Further, the mobile terminal device 100 may be configured to unlock itself when it is detected that the mobile terminal device 100 is connected to the previously paired cradle 200. As described above, a configuration using a biometric system in cooperation with a PC or the like may be adopted.

Further, the mobile terminal device 100 may be configured to transmit the unlocking request to the information management device 300 by the wireless communication at arbitrary timing rather than transmitting the unlocking request to the information management device 300 by the wire connection when the mobile terminal device 100 is connected to the cradle 200. In this case, the control section 301 transmits the unlocking request to the information management device 300 at, e.g., fixed time intervals. Furthermore, the control section 301 adds the state information to the unlocking request and transmits it to the information management device 300. In this case, the information management device 300 determines whether unlocking the mobile terminal device 100 is appropriate based on the received state information, and transmits the unlocking signal to the mobile terminal 100 device when unlocking is determined to be appropriate.

It is to be noted that the functions described in the foregoing embodiment may be realized by not only using hardware but also reading a program in which each function is written to a computer by using software. Moreover, each function may be configured by appropriately selecting the software or the hardware.

It is to be noted that the present invention is not restricted to the foregoing embodiment as it is, and it can be carried out on the embodying stage by modifying constituent elements without departing from a gist thereof. Additionally, various inventions can be formed by appropriately combining constituent elements disclosed in the foregoing embodiment. For example, some of all constituent elements shown in the embodiment may be deleted. Further, constituent elements in different embodiments may be appropriately combined. In particular, although the description has been given on the assumption of a hospital were personal information is managed and greater importance is given to privacy issues, it is needless to say that management is important in operation information or personal information management and the present invention can be exploited in various workplaces, stores, airports, harbors, factories, construction or building sites, households, or the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A mobile terminal device comprising:
an operation input section which accepts operations;
a memory section which previously stores a list of states of the mobile terminal device during use as locking conditions to determine a state at the time of limiting an operation of the mobile terminal device;
a state determining section which generates state information in accordance with a state of the mobile terminal device;
a function limiting section which determines whether the state information meets the locking conditions, and switches the mobile terminal device to a locked state to limit an operation of the operation input section, when the state information is determined to meet the locking conditions; and
a communication section which communicates with a host device,
wherein the memory section stores the locking conditions transmitted from the host device,
wherein the communicating section is connected to the host device through a network, and detects connection to a cradle which supplies electric power to the mobile terminal device is established, and
the mobile terminal device further comprises:
an unlocking request section which transmits an unlocking request to the host device when establishment of the connection to the cradle is detected; and
a control section which controls the function limiting section to cancel the locked state when an unlocking signal transmitted from the host device is received.

2. The device according to claim 1,
wherein the state determining section generates time information indicative of an elapsed time from disconnection from the cradle as the state information, and
the function limiting section determines whether the elapsed time from the disconnection from the cradle has reached a predetermined time indicated by the locking conditions based on the state information, and switches the mobile terminal device to the locked state when the elapsed time is determined to have reached the predetermined time.

3. The device according to claim 1, further comprising a power supply section which charges with electric power supplied from the cradle,
wherein the state determining section generates time information indicative of an elapsed time from interruption of charging as the state information, and
the function limiting section determines whether the elapsed time from the interruption of charging has reached a predetermined time indicated by the locking conditions based on the state information, and switches the mobile terminal device to the locked state when the elapsed time is determined to have reached the predetermined time.

4. The device according to claim 1,
wherein the state determining section generates positional information indicative of a position of the mobile terminal device as the state information, and
the function limiting section determines whether the position is a predetermined position indicated by the locking conditions based on the state information, and switches the mobile terminal device to the locked state when the position is determined not to be the predetermined position.

5. The device according to claim 1,
wherein the state determining section generates information indicative of a moving path of the mobile terminal device as the state information, and
the function limiting section determines whether the moving path is a predetermined route indicated by the locking conditions based on the state information, and switches the mobile terminal device to the locked state when the moving path is determined not to be the predetermined route.

6. The device according to claim 1,
wherein the state determining section generates information indicative of a login user of the mobile terminal device as the state information, and
the function limiting section determines whether the login user is a predetermined user indicated by the locking conditions based on the state information, and switches the mobile terminal device to the locked state when the login user is determined not to be the predetermined user.

7. A mobile terminal device comprising:
an operation input section which accepts operations;
a memory section which previously stores a list of states of the mobile terminal device during use as locking conditions to determine a state at the time of limiting an operation of the mobile terminal device;
a state determining section which generates state information in accordance with a state of the mobile terminal device; and
a function limiting section which determines whether the state information meets the locking conditions, and switches the mobile terminal device to a locked state to limit an operation of the operation input section, when the state information is determined to meet the locking conditions;
wherein the state determining section generates information indicative of the number of other mobile terminal devices present within a predetermined distance of the mobile terminal device as the state information, and
the function limiting section determines whether the number is equal to or more than a predetermined number indicated by the locking conditions based on the state information, and switches the mobile terminal device to the locked state when the number is determined to be equal to or more than the predetermined number.

8. An information management system comprising an information management device and a mobile terminal device which communicates with the information management device, the system comprising:
a locking condition transmitting section which transmits locking conditions for use in determining whether the mobile terminal device locks itself from the information management device to the mobile terminal device;
a memory section which stores in the mobile terminal device the locking conditions transmitted from the information management device to the mobile terminal device;
an operation input section which accepts an operation to the mobile terminal device;
a state determining section which generates state information in accordance with a state of the mobile terminal device;
a function limiting section which determines whether the state information meets the locking conditions, and switches the mobile terminal device to a locked state to limit an operation of the operation input section, when the state information is determined to meet the locking conditions;
an unlocking request section which transmits an unlocking request from the mobile terminal device to the information management device when establishment of connection to a cradle is detected;
an unlocking signal transmitting section which transmits an unlocking signal to cancel the locked state of the mobile terminal device from the information management device to the mobile terminal device when the information management device receives the unlocking request; and
a control section which controls the function limiting section to cancel the locked state of the mobile terminal device when the unlocking signal is transmitted from the information management device to the mobile terminal device.

9. A control method of a mobile terminal device comprising:
an operation input section which accepts operations;
a memory section which previously stores a list of states of the mobile terminal device during use as locking conditions to determine a state at the time of limiting an operation of the mobile terminal device;
a state determining section which generates state information in accordance with a state of the mobile terminal device;
a function limiting section which determines whether the state information meets the locking conditions, and switches the mobile terminal device to a locked state to limit an operation of the operation input section when the state information is determined to meet the locking conditions;
a communication section which communicates with a host device; and
a controller,
wherein the memory section stores the locking conditions transmitted from the host device,
wherein the communicating section is connected to the host device through a network, and detects when connection to a cradle which supplies electric power to the mobile terminal device is established, and
wherein the controller transmits an unlocking request to the host device when establishment of the connection to a cradle is detected, and controls the function limiting section to cancel the locked state when an unlocking signal transmitted from the host device is received.

\* \* \* \* \*